United States Patent [19]

Paluch

[11] Patent Number: 4,856,548

[45] Date of Patent: Aug. 15, 1989

[54] RESUSCITATION VALVE

[76] Inventor: Bernard R. Paluch, 1607 Cedar La., Mount Prospect, Ill. 60056

[21] Appl. No.: 166,207

[22] Filed: Mar. 10, 1988

[51] Int. Cl.$^4$ .............................................. A62B 9/02
[52] U.S. Cl. ............................. 137/102; 128/205.24; 137/516.25
[58] Field of Search .................. 137/102, 854, 516.25; 128/203.11, 205.13, 205.24

[56] References Cited

U.S. PATENT DOCUMENTS

| | | | |
|---|---|---|---|
| 3,063,461 | 11/1962 | Rudolph | 137/102 |
| 3,356,100 | 12/1967 | Seeler | 137/102 |
| 4,204,555 | 5/1980 | Durling | 137/102 |
| 4,449,525 | 5/1984 | White et al. | 128/203.11 |
| 4,733,919 | 3/1988 | Jacobs et al. | 137/102 |

FOREIGN PATENT DOCUMENTS 89883 10/1960 Denmark ........................ 128/205.13

Primary Examiner—Stephen M. Hepperle
Attorney, Agent, or Firm—John G. Tolomei

[57] ABSTRACT

A resuscitation valve uses a pair of thin membrane valve elements that are spaced apart about an exhaust passage to provide increased reliability and simplify construction and fabrication. The resuscitation valve is of the nonrebreathing type and includes a valve housing that defines a chamber and an inlet port and patient port in communication therewith. The housing also defines an exhaust port. A center body is positioned in the housing and has a hollow interior communicating the chamber with the exhaust port. First, second, and third valve seats are located between the exhaust port and the center body, the inlet port and the chamber, and at one end of the center body, respectively. The pair of resilient membranes act as valve elements and one membrane closes the outlet port in response to negative pressure at the patient port by sealingly contacting the first valve seat; the second membrane closes the inlet port in response to pressure at the patient port that exceeds the pressure at the inlet port by sealingly contacting the second valve seat, and also closes the exhaust passage when positive pressure at the inlet port exceeds positive pressure inside the center body by sealingly contacting said third valve seat. A center body separates the valve elements and can be used to facilitate simple-snap together construction of the valve. The valve design is particularly suited for the fabrication of a disposable resuscitation valve.

22 Claims, 2 Drawing Sheets

RESUSCITATION VALVE

FIELD OF THE INVENTION

The field of this invention relates broadly to breathing equipment. More specifically this invention relates to resuscitation valves having non-rebreathing operation that are suitable for use in manually or automatically operated resuscitation equipment.

BACKGROUND OF THE INVENTION

Resuscitation describes the use of external efforts to assist or restore the breathing of a person whose breathing has ceased or become impaired, by forcing oxygen containing gas into the lungs of the person under pressure, and then providing an interval of time for the lungs to deflate and gas to escape. Some forms of resuscitation such as mouth to mouth require no form of specialized resuscitation equipment. However where available it is generally preferred that resuscitation be performed with the assistance of specially designed resuscitation equipment.

A resuscitation device in widespread use is the "squeeze-bag" type resuscitator. This device has a resilient, manually compressible bag that stores a quantity of oxygen containing gas, usually air or oxygen enriched air, which is forced out of the bag under pressure by squeezing the bag. When squeezing of the bag ceases and the bag is released it regains its shape and in the process refills itself with gas. Gas from the bag is ultimately delivered to the victim or patient through an inhalation mask that covers the nose and mouth of the patient, or through another device such as an endotracheal or tracheostomy tube. Modern resuscitation devices use a resuscitation valve to direct gas from the bag and into the patient.

Another type of resuscitation device uses a pneumatically-actuated cylinder and piston to depress the sternum while synchronizing the delivery of gas to the patient's lungs.

The resuscitation valve in these devices controls gas flow between the patient and the valve. When the bag is compressed the valve performs the basic function of directing gas from the bag into the mask. In addition, the valve provides a non-rebreathing function that vents gas exhaled by the patient to the atmosphere and prevents the exhaled gas from entering the bag. Should the patient begin unassisted breathing the valve permits inhalation of gas from the bag only. Of course, the valve must not vent gas from the bag when inspiratory resistance in the patient causes airway pressure to rise. Accordingly the resuscitation valve must perform a multiplicity of functions.

These multiple functions provide numerous advantages and are therefore found in a variety of resuscitation devices that include mouth to mask resuscitation equipment as well as bag type resuscitators. A major function of a resuscitation valve is isolation of the gas supply source from the patient. With the valve in place exhaled air, liquids or vomitus from the patient will not enter the bag or in the case of mouth-to-mask resuscitation devices, the person supplying the gas. Another function of the valve is that it must cause the patient to inhale gas only from the bag. This function is particularly helpful when administering oxygen-enriched gas to the patient by preventing the patient from rebreathing exhaled gas with its lower oxygen concentration and higher carbon dioxide concentration.

For a resuscitation valve to provide satisfactory service it must meet a number of criteria. The valve must operate reliably. Reliable operation demands that a variety of valve elements perform the necessary sealing functions while not unduly restricting gas flow or burdening normal breathing by the patient. It is particularly desirable that valve elements needing a relatively large degree of movement to achieve sealing be avoided since the need for movement is a source of possible malfunction. A number of more recent valve designs use flexible membranes to achieve sealing, however reliability may be impaired when these membranes require excessive deformation or flexing to open and close.

Furthermore, the valve elements must be compact so that the overall size of the valve remains small in relation to the rest of the resuscitation apparatus. Ideally the valve would also be capable of continued operation when liquids and vomitus expelled by the patient enter the valve. As a result, resuscitation valves that provide all or most of these desired functions tend to be complicated in construction and relatively high in price.

Consequently, the considerable cost associated with the majority of resuscitation valves has dictated their reuse. Before reuse, a complete cleaning and disinfection of the valve must be done to assure sanitary conditions and proper operation. Thorough cleaning of a resuscitation valve means at least a partial disassembly. Although the need for disassembly and cleaning of the valve is a disadvantage in itself, it poses additional hazards since the valve may be unknowingly damaged or reassembled improperly during the cleaning process. As a result an additional testing procedure is needed to make sure that the resuscitation devices are operating properly after cleaning. The need to clean the resuscitation valves also adds to the less obvious but substantial problem of resuscitator equipment loss.

Portable resuscitators are in common use and found in many hospital departments, ambulances, paramedic units, clinics, first aid kits, and doctor's offices. In a typical hospital situation, the respiratory care or central supply unit is responsible for cleaning all resuscitation equipment. Since a number of departments use bag resuscitators they all depend on the department doing the cleaning to have an adequate surplus of bags to meet their needs. When removal for cleaning leaves an inadequate supply of bags in a given area, bag stealing between departments commonly occurs and can lead to a shortage of bags in a department. Unfortunately bag stealing does not stop with interdepartmental raiding. Other bag users that are in and out of the hospital may see the hospital as a convenient source of resuscitation bags and take hospital-owned bags.

It has been recognized that disposable resuscitation devices would have the advantage of not requiring cleaning. However, some disposable devices that have been proposed do not provide all of the functions of the reusable valves. In addition, at least one such valve incorporates a mask integral with the valve so that the cost of such a device is still rather high.

DISCLOSURE STATEMENT

U.S. Pat. No. 3,796,216 issued to Schwarz on Mar. 12, 1974 describes a disposable resuscitation device that includes an inhalation mask and bag as a single unit. The valve uses a flapper valve disposed between and alternately in contact with an exhalation port to block gas flow therethrough when the bag is squeezed and in contact with an inlet port when the patient is exhaling, to prevent exhalation into the bag.

U.S. Pat. No. 4,374,521 issued to Nelson et al. on Feb. 22, 1983 generally shows a full function resuscitation valve of the non-rebreathing type used on a bag type resuscitator.

U.S. Pat. No. 3,556,122 issued to Laerdal on Jan. 19, 1971 and U.S. Pat. No. 3,356,100 issued to Seeler on Dec. 5, 1967 are directed to resuscitation valves having a single deformable membrane that cooperates with a pair of valve seats to provide a dual function of sealing an exhaust port when pressurized gas is directed to a patient and sealing the inlet port to prevent exhalation by the patient into the pressure source.

U.S. Pat. No. 3,473,529 issued to Wallace on Oct. 21, 1969 shows a resuscitation valve in a bag-type resuscitation device that consists of a solid disc and opposed inlet and outlet ports for delivering and receiving gas to and from a patient. The disc slides on a center shaft and a spring biases the disc against the inlet port in the absence of gas flow out of the bag.

U.S. Pat. No. 3,993,059 issued to Sjostrand depicts a solid disc between two valve seats in a lung ventilator device.

The operation of the disc is not clearly described, but it appears to operate in a similar manner to that of the Wallace reference.

British Pat. No. 1,280,983 depicts a valve structure having two flapper valves for regulating gas flow into and out of a main valve body and an internal conduit through which gas flows and which projects at least partially across a mouthpiece conduit.

U.S. Pat. No. 1,880,998 shows a valve that is similar in structure to the British patent 1,280,983.

U.S. Pat. No. 3,519,012 shows a valve having an inner conduit projecting completely past one of the inlet/outlet conduits, a flapper valve mounted at the end of the conduit, and gas flow out of the valve which is restricted to an annular passage between the valve body and the inner conduit. This patent is cited for its non-analogous use of an extended inner conduit.

U.S. Pat. No. 4,222,207 is not a non-rebreathing device but shows a one way flapper valve supported on one side by a central rib.

U.S. Pat. No. 4,456,016 shows an inhalation device that uses a two piece snap together construction wherein the flapper valve disc is secured in place by assembly of the valve.

Italian Pat. No. 452,112 shows a device for a tracheotomy patient having a trap assembly used as a fluid or phlegm collector.

BRIEF DESCRIPTION OF THE INVENTION

Accordingly it is an object of this invention to provide a resuscitation valve that provides non-rebreathing operation and consists of simple valve elements.

It is a further object of this invention to provide an arrangement suitable for the construction a disposable non-rebreathing type resuscitation valve.

A yet further object of this invention is to provide a resuscitation valve having relatively fixed valve elements that need only a small amount of deflection to open and close.

Another object of this invention is to provide a resuscitation valve having reliable operation that is not easily disrupted by the presence of liquid or solid material.

A more general object of this invention is to provide a method for preventing loss of resuscitation devices that use a disposable resuscitation valve.

This invention is the first resuscitation valve having a design that can be assembled in a simple manner from inexpensive elements while providing highly reliable and effective pressurization and non-rebreathing functions even under adverse operating conditions. The invention achieves these goals by using two simple valve elements on either side of an exhaust passage, for controlling gas flow through a pair of inlet and outlet ports. The valve elements in simplest form can consist of flexible discs that are centrally supported and each using only an outer edge of the disc for contacting a valve seat and establishing a seal therewith. One of the valve elements serves a double function. It prevents exhalation by the patient into the source of the resuscitation gas when the valve is one mode of operation, and alternately blocks the exhaust of resuscitation gas in the other mode of operation so that gas is forced into the patient's lungs.

In a broad embodiment the invention is a resuscitation valve that includes a valve housing, an exhaust passage and a pair of resilient valve elements. The resilient valve elements are located at opposite ends of the exhaust passage and fixed at least about their centers with respect to the valve housing. The valve housing defines a chamber, an inlet port, a "patient" port in communication with the chamber, and an exhaust port. The patient connects to the valve at the patient port. The exhaust passage is located within the housing and has a first end in closed communication with the exhaust port. The other end of the exhaust passage communicates with the chamber. One of the valve members cooperates with a first valve seat positioned between the exhaust port and the passage to occlude the exhaust port in response to negative pressure at the patient port, i.e., inhalation by the patient. The terms positive pressure and negative pressure as used herein are taken relative to atmospheric pressure. The other valve member is positioned between the second and third valve seats. The second and third valve seats are located between the inlet port and the chamber and the passage and the chamber, respectively. When pressure in the patient port exceeds pressure at the inlet port—the patient is exhaling—the second valve member sealingly contacts the second valve seat to occlude the inlet port. Forcing pressurized gas from the bag creates a positive pressure at the inlet port which causes the second valve element to sealingly contact the third valve seat and occlude the exhaust passage, thus forcing gas flow through the patient port and into the patient.

Other aspects, embodiments, and details of this invention are presented in the following detailed description.

DETAILED DESCRIPTION OF THE INVENTION

Figure 1:
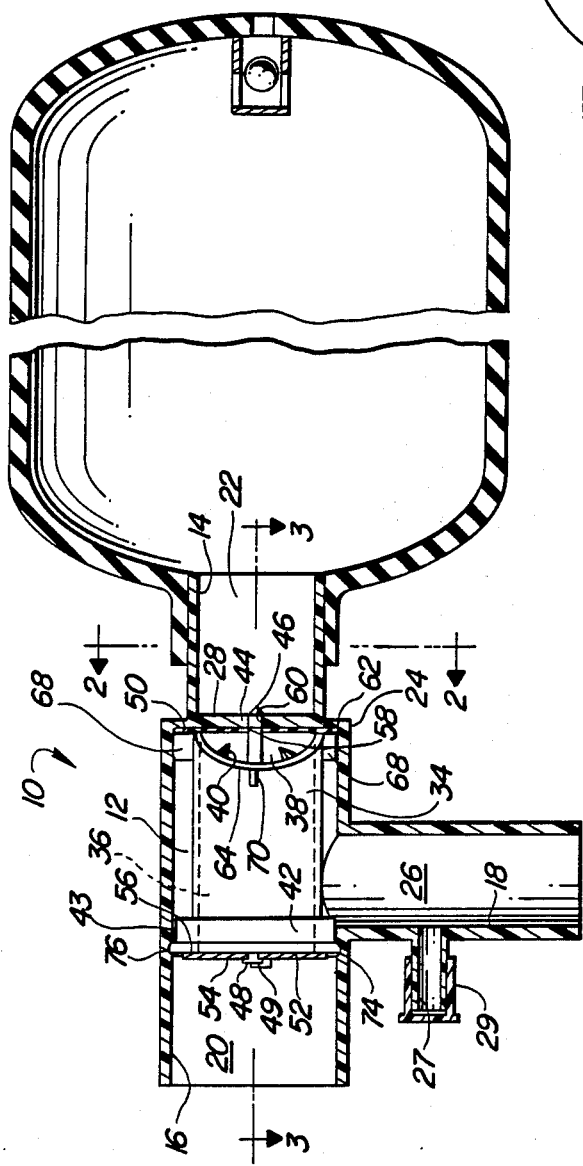
FIG. 1 is a partial cross section of the valve of this invention attached to a resuscitation bag and showing the valve housing in full cross section along with a full center body inside the housing.

Referring first to FIG. 1 a valve housing 10 is shown. Housing 10 defines a chamber 12 in its center, an inlet port 14, an exhaust port 16 and a respiration port 18. Chamber 12 and exhaust port 16 are part of a large diameter bore 20 and inlet port 14 is part of a small diameter bore 22. Bore sections 20 and 22 together make an axially aligned step bore defined by a continuous cylindrical portion housing 10 and having a step portion 24. The housing also has a cylindrical portion that defines a respiration port 18 which is part of a bore 26. Bore 26 is a branch bore that is in open communication with the stepped bore and that intersects the centerline of the stepped bore in large diameter section 20. A center bar 28 spans the diameter of inlet port 14. The remainder of bore 22 is open on either side of bar 28 for communicating bore 22 with chamber 12.

Housing 10 is preferably designed of inexpensive plastic materials to suit the contemplated sizes of the apparatus which will be attached thereto. Thus the outer diameter of inlet port 14 is typically sized to match the inside diameter of a typical connection 30 for a squeeze-bag 32. Similarly, respiration port 18 has an outside diameter that will accomodate a respiration mask or tracheal tube (not shown). Since it may not be possible or desirable to design separate valve housings to suit all sizes and combination of air bag and mask connections, the use of sleeve type adapters (not shown) to allow use of the valve with resuscitation devices of varying outlet dimensions is contemplated. Although there is frequently no need for attachment to the exhalation port, its outside diameter can be adjusted in a similar manner when necessary.

A small port 27 is shown in communication with respiration port 18. This port may be used to add pure oxygen to the inhalation mask for the purpose of elevating the oxygen content of the gas that the patient inhales. Alternately, it allows a measurement or monitoring of the pressure of the gas delivered to the patient. When not in use it is occluded with a suitable cap 29.

Within the housing a center body in the form of an exhaust tube 34 is shown occupying chamber 12. The center body will have a substantially hollow interior which provides an exhaust passage 36. The term substantially hollow is used to describe the interior of center body since in its preferred form a full diameter chord member 38 traverses the middle of the center body over its entire length and the center body may include one or more partial ribs 40 projecting radially inward from the inside of the center body. The ribs 40 and chord member 38 lend structural support to a hereinafter described valve element, but do not unduly restrict air flow through the substantially hollow interior. Thus, exhaust passage 36 includes the open interior space on both sides of member 38. Both ends of the exhaust passage are open for gas flow therethrough. A left end of the passage, denoted 42 communicates directly with exhaust port 20, and a right end, 44, of the passage communicates with chamber 12. Tube 34 has an outer diameter that is substantially smaller than the inside diameter of chamber 12. The different diameters establish an annular flow area for communicating patient port 18 with exhaust passage 36. Left end 42 of the center body has an enlarged diameter portion 43 that blocks direct communication between chamber 12 and exhaust port 20 by occluding the annular flow area.

A Pin 46 extends axially from the center of chord member 38 at right end 44 and another pin 48 having an outer shoulder 49 extends axially from the center of chord member 38 at left end 42. Pin 46 supports a valve member 50 and pin 48 supports a valve member 52. Both valve members are resilient membranes of continuous curvature and in the preferred form of the invention are simple, flexible rubber or plastic discs having a center hole through which the pin passes. A preferred material for the disc is siliconized latex rubber having a thickness of from 0.010 to 0.025 inches, with a thickness of 0.015 inches being particularly preferred. Pins 46 and 48, at least in part, fix the centers of discs 50 and 52 relative to the housing 10.

A center hole 54 fits around the small diameter portion of pin 48 and the shoulder portion of pin 48 keeps disc 52 centered over the end 42 of exhaust passage 36 which is otherwise open. Disc 52 extends radially past the periphery of exhaust passage 36 and has its outermost portion overlying a valve seat 56 which consists of an annular surface on tube 34.

At the opposite end of the center body pin 46 passes through a central hole 58 in disc 50 and is received by a hole 60 defined by bar 28. The right side of chord member 38 and the left side of bar 28 restrain disc 50 and fix the disc relative to housing 10 about a vertical line of support that includes its center. The outer edge of disc 50 extends radially past the openings between inlet port 22 and the chamber and past the main outer wall of tube 34. A face 78 of disc 50 has an outer portion positioned next to an annular valve seat 62 which is defined by the surface of step portion 24. Disc 50 can be bent about its line of support to contact a valve seat 64 comprising the end surface of center body 34.

Figure 2:
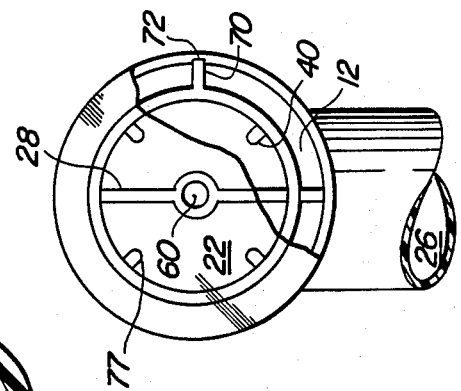
FIG. 2 is a front view of FIG. 1 taken along line 2—2 with a broken section on one side and the resuscitation bag omitted.

In its preferred form the center body like the housing is made of inexpensive plastic material and moreover is designed for snap-together construction. At end 42, tube 34 has a rib 74 that extends circumferentially around the enlarged diameter portion 43 and engages an undercut 76 that extends circumferentially around bore 20. As depicted by FIG. 1 a pair of fins 68 extend from the outer surface of the center body and stop just short of contacting the inside of bore 20. Another pair of fins 70 extend radially outward from the sides of center body 34, and as shown by the partial section of FIG. 2, each fin 70 is received in a groove 72 formed in the inner surface of housing 10. Fins 68 and 70 and the grooves 72 may be alternately located on the inner surface of housing 10 and the center body 34. FIG. 2 also shows an arrangement of ribs 77 that are used to support disc 50 in a manner similar to ribs 40 and hereinafter described. Fins 70 and groove 72 align chord member 38 and bar 28 to cause disc 50 to bend about its centerline only, thereby facilitating proper sealing of disc 50 against the exhaust tube.

The valve is easily assembled by first placing discs 50 and 52 over pins 46 and 48, and then sliding the exhaust tube into the housing through the exhaust port. The exhaust tube has a wider diameter across fins 70 than the inside diameter of bore 20. The greater overall diameter of fins 70 prevents the tube from being inserted into the housing unless it is in the proper rotational position. As the tube is slid into place all of the fins maintain alignment of the tube so that pin 46 is received in hole 60. When the front of disc 50 begins to contact the left side of center bar 28, rib 74 registers within undercut 76 to secure the exhaust tube 34 in proper axial alignment with respect to housing 10. Engagement of rib 74 in undercut 76 forms a seal therebetween that further prevents the communication of gas between chamber 12 and exhaust port 16. Additional details of rib 74, undercut 76, fins 70, and slot 72 can be seen in FIG. 3. FIG. 3 again shows center body 34 positioned in housing 10. Fin 70 is at the end of groove 72 which it occupies when the center body is fully advanced in the housing after assembly.

Figure 3:
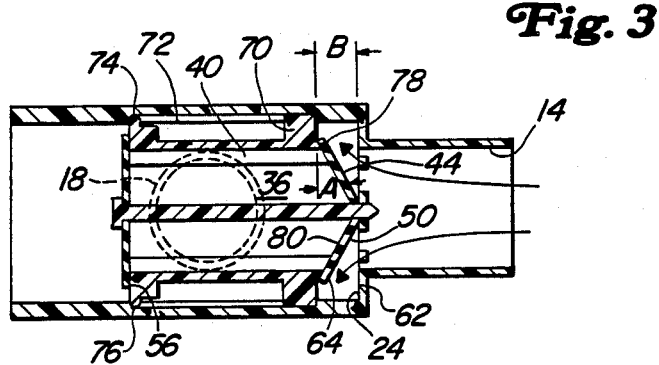
FIG. 3 is a section taken along lines 3—3 of FIG. 1 showing a pair of valve elements in a first position.

As can also be seen from FIG. 3, right end 44 of the tube has an angled profile that provides a progressive double taper across the front of the tube 34 with trailing edges on each side of the tube that converge in a central ridge defined by chord member 38. FIG. 3 shows the taper having a linear profile, however it is also possible to provide a convex or concave profile to the taper. When a straight taper is used it is preferred that it have an included angle A in a range of 15 to 20 degrees. These angles provide an opening, having a width indicated by dimension B, between the sides of the center body and step 24 which has been found to provide ample flow area for the ingress of gas from inlet port 14. FIG. 3 shows disc 50 deflected away from step 24 and in contact with valve seat 64. Dimension B should not be overly wide otherwise excessive deflection will be required for disc 50 to contact valve seat 64 and/or disc 50 will have insufficient overlap with seat 64 to establish a reliable seal.

Turning then to the operation of the valve, the position of disc 50, as shown in FIG. 3, corresponds with a forced ventilation mode of operation for the valve. In this mode of operation air from a suitable source of pressure, such as the squeeze bag shown in FIG. 1, i forced into the lungs of the patient. Air flow from the bag creates relatively high pressure at inlet port 14 which acts on face 78 of disc 50 to deflect the disc away from seat 62. This air is then directed to the patient via chamber 12 and respiration port 18. The presence of a positive gas pressure at the inlet port will deflect disc 50 so that a face 80 seals against valve seat 64 and prevents the loss of ventilating pressure through exhaust passage 36. The aforementioned ribs 40 as well as chord member 38 support disc 50 so that pressure on face 78 cannot deform the membrane and force it into exhaust passage 36 thereby causing possible malfunction of the valve. Disc 50 must be of sufficient diameter so that when deformed it will cover the entire face of valve seat 64.

Figure 4:
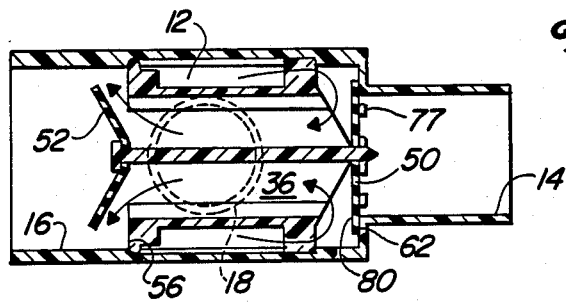
FIGS. 4 and 5 are similar views of the valve as shown in FIG. 3 with the valve elements in different operational positions.

After the desired volume of gas is delivered into the patient, the bag is released, inlet gas flow stops, and the patient exhales, expelling gas under pressure from his or her lungs, thereby creating a relatively higher pressure in patient port 18 and chamber 12 as opposed to inlet port 14 and exhaust passage 36. When inlet pressure drops and exhalation begins, the formerly higher relative pressure on disc face 78 dissipates and disc 50 rebounds to the position shown in FIG. 4. Higher pressure now acting on face 80 forces disc 50 against seat 62 to prevent exhaled gases from entering inlet port 14. During exhalation the bag is refilled or other resuscitation device is cycled to ready it for the next gas delivery phase. In many device arrangements, refilling of the bag will produce a vacuum at inlet port 14. This vacuum and the pressure of exhalation can create a high pressure differential between faces 78 and 80 of disc 50. Previously described ribs 77 support disc face 78 to prevent a high pressure differential from forcing the disc into inlet port 16 and again causing a possible malfunction of the valve. With disc 50 against seat 62 exhaled gas passes from chamber 12 into exhaust passage 36 and deflects disc 52 away from seat 56, thereby allowing the exhaled gas to pass into exhaust port 16 and out of the valve.

Figure 5:
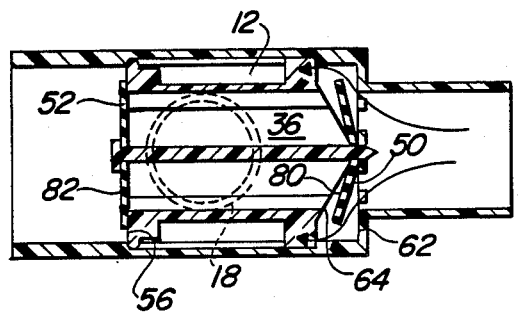

Disc 52 comes into sealing operation, represented by FIG. 5, when the patient inhales by his or her own effort. An inhalation effort by the patient creates a partial vacuum in patient port 18, chamber 12 and exhaust passage 36. Relatively higher pressure acting on a face 82 of disc 52 presses the disc against seat 56 so that air is not inhaled through exhaust port 16. Instead, only gas from the pressurization device is available through inlet port 14. Gas flow from the inhalation port deflects disc 50 away from seat 62 as the gas flows into chamber 12 and through patient port 18. The negative pressure created by the patient's inhalation deflects disc 50 to an intermediate position somewhere between valve seats 62 and 64.

As explained in the background of this invention it is common for the patient to expel liquid and particulate material during resuscitation. This material can cling to the valve seats and valve elements causing the valve elements to stick or not establish a seal. The internal arrangement of this valve can aid in eliminating this problem by keeping the valve elements positioned out of direct alignment with the patient port. By arranging the valve elements out of direct alignment, matter expelled by the patient is likely to impact on some other surface and not interfere with the valve operation. The center body also assists in removing particulate or liquid matter from the fluid flow by forcing exhaled gases to travel around it so that ballistic forces and centripedal accelerations will deposit such matter on surfaces of the housing and center body located upstream of the valve elements. For this purpose the end of the centerbody opposite the inlet port should be axially aligned and in close proximity to the patient port. With the center body so aligned its length can be increased to provide a longer flow path between the patient port and disc 50. Preferably the center body will have enough length to keep both valve elements out of direct alignment with the patient port, and more desirably it will have an axial length at least equal to twice the diameter of the patient port. It is also preferred that the center body be aligned with the primary axis of the patient port and that the center body be wider than the inner diameter of the patient port so that the projected opening of the patient port lies completely on the center body.

Although the resuscitator valve of this invention has numerous advantages over prior art valves when considered by itself, it is most beneficially used as part of a comprehensive loss prevention program for portable resuscitation equipment. By using the arrangement of this invention to produce an inexpensive, disposable, resuscitation valve it is no longer necessary, for cleaning purposes, to remove the resuscitation equipment that uses the valve from the area in which it is used. Therefore, in the case of bag-type resuscitators, a definite inventory of the bags can be maintained and more closely controlled in each location where they are used. Since the valves are relatively inexpensive, a surplus of valves may be kept with an inventory of bags to insure adequate availability of clean valves. The valve of this invention, when assembled in the preferred manner, is not suitable for reuse since it is not readily disassembled for cleaning. Thus there is a disincentive to acquire reusable bags with a disposable valve since the bag will be useless after a single use unless additional valves are also available. This valve also allows a procedure to be established for preventing bag loss when a patient is transferred between departments or attending parties. For example when a patient is brought into a hospital by a paramedic unit and a bag-type resuscitator is in use by the paramedics, hospital personnel and the paramedics can swap valves while leaving the contaminated valve on the patient for continued use. This valve swap procedure can be used interdepartmentally in the same manner. Therefore with the tighter inventory controls and the valve swap program made possible by the valve of this invention, a number of the problems associated with the use and availability of portable resuscitation equipment are overcome.

What is claimed is:

1. A resuscitation valve of the non-rebreathng type for forcing gas into the lungs of a person under pressure, said valve comprising:
    a valve housing, said housing defining a chamber, an inlet port and a patient port in communication with said chamber, and an exhaust port;
    an exhaust passage located within said housing having a first end in closed communication with said exhaust port and
    a second end communicating said passage with said chamber;
    a first valve seat between said exhaust port and said passage;
    a first valve element comprising a thin resilient membrane having at least its center fixed relative to said housing and positioned to occlude said exhaust port by sealingly contacting said first valve seat in response to negative pressure in said patient port;
    a second valve seat between said inlet port and said chamber;
    a third valve seat arranged about the second end of said passage and located opposite said first valve seat;
    a second valve element comprising a thin, relatively flat, and resilient membrane having at least its center fixed relative to said housing and positioned to occlude said inlet port by sealingly contacting said second valve seat with an outer portion of said second valve element when pressure in said patient port exceeds pressure in said inlet port and occlude said second end of said exhaust passage when positive pressure in said inlet port exceeds positive pressure in said exhaust port be sealingly engaging said third valve seat with an outer portion of said second valve element;
    and a chordal member extending parallel to said second valve element and positioned for contact with said second valve element such that said second valve member is bent about said chordal member when said second valve element occludes at least one of said inlet port and said second end of said passage.

2. The valve of claim 1 wherein a tubular member defines said exhaust passage.

3. The valve of claim 2 wherein said tubular member is in the axial flow path of said patient port and both valve elements are removed from the axial flow path of said patient port.

4. The valve of claim 1 wherein both of said valve elements comprise relatively flat, flexible discs.

5. The valve of claim 2 wherein said valve members are fixed to said tubular member.

6. The valve of claim 2 wherein said tubular member is adapted to be slid into place in said housing and means are provided on said tubular member and said housing for retaining said tubular member in said housing after it has been slidably inserted therein.

7. The valve of claim 6 wherein said means includes a rib on one of said housing and said tubular member and a groove for receiving said rib on the other of said tubular member and said housing.

8. The valve of claim 1 wherein said second end of said exhaust passage has a double taper that converges in a central ridge to form said third valve seat and said chordal member.

9. A resuscitation valve of the non-rebreathing type for forcing gas into the lungs of a person under pressure, said valve comprising:
    a valve housing defining a chamber, an inlet port and a patient port in communication with said chamber, and an exhaust port;
    a center body positioned in said chamber and extending between said inlet port and exhaust port, said center body having an at least partially hollow interior communicating said chamber with said exhaust port;
    a first valve seat between said exhaust port and the interior of said center body;
    a second valve seat between said inlet port and said chamber;
    a third valve seat located at a first end of said of said center body said first end of said center body having a double taper that provides said third valve seat and converges to form a central chordal member that extends across said first end of said center body;
    a pair of thin resilient membranes separated by and fixed with respect to said center body with a first one of said membranes being positioned to occlude said exhaust port in response to negative pressure at said patient port by contact with said first valve seat and a second one of said membranes having a relatively flat disc shape and being positioned between said first and second valve seats to occlude said inlet port when pressure at said patient port exceeds pressure at said inlet port by contact with said second valve seat and occlude said at least partially hollow interior of said center body when positive pressure at said inlet port exceeds positive pressure in said center body by bending about said chordal member and contacting said third valve seat.

10. The valve of claim 9 wherein said inlet port and exhaust port are in axial alignment and the central axis of said patient port intersects the axis of said inlet and outlet ports.

11. The valve of claim 9 wherein the axial flow path of said patient port intersects the outside of said center body.

12. The valve of claim 9 wherein both of said resilient members are at least partially secured to said center body.

13. The valve of claim 9 wherein said center body is insertable into said housing.

14. The valve of claim 11 wherein the width and axial length of said center body exceeds the diameter of said patient port.

15. The valve of claim 9 wherein a gas connection is located on said housing in direct communication with said patient port.

16. A resuscitation valve of the non-rebreathing type, said valve comprising:

a valve housing having a continuous cylindrical portion defining a stepped bore, and an intersecting cylindrical portion defining a branch bore that intersects a large diameter portion of said stepped bore, said housing including an inlet port at the small end of said stepped bore, an exhaust port at the large end of said stepped bore, a step abruptly changing the diameter of said stepped bore, a first valve seat defined by said step, a center bar traversing said smaller bore at said step and a patient port defined by said branch bore and communicating with a portion of said stepped bore located between said inlet and exhaust ports;

an exhaust tube positioned in and having a substantially smaller outer diameter than the larger inner diameter of said stepped bore, said exhaust tube having an at least partially hollow interior and axial openings at both ends, the first end of said tube having doubly tapered sides forming a second valve seat and converging in a central ridge traversing the center of said exhaust tube at said first end, said ridge having a position immediately opposite to and parallel with said center bar and the second end of said tube having means for occluding the space between the inside of the step bore and the outside of said tube and a third valve seat bordering the periphery of the opening at said second end;

means for guidingly inserting said tube in said housing;

a first substantially flat resilient disc fixed between said central ridge and center bar, said first disc having sufficient flexibility for alternately contacting said first and second valve seats for sealing contact therewith;

a second substantially flat resilient disc positioned across said second end of said tube and having sufficient flexibility for sealingly contacting said third valve seat; and means for fixing the central portion of said second disc with respect to said tube.

17. The valve of claim 16 wherein both of said discs are at least in part secured in said housing by said center body.

18. The valve of claim 17 wherein said central ridge has a pin extending outward therefrom that passes through a support hole in said first disc and is received by an aperture defined in said center bar.

19. The valve of claim 18 wherein said second disc is secured to a central pin extending from the second end of said tube.

20. The valve of claim 19 wherein a slot in the inner surface of said valve body receives a fin extending radially from said tube to provide said means for guidingly inserting said tube in said housing.

21. The valve of claim 20 wherein an undercut extending circumferentially about the large diameter portion of said step bore engagingly receives a rib that projects radially outward from said means for occluding the space between said tube and said step bore to hold said tube in said housing.

22. The valve of claim 21 wherein said central ridge runs parallel to the axis of said branch bore and the projection of said patient port lies completely on the outer surface of said tube.

* * * * *